United States Patent
Cordery et al.

(10) Patent No.: US 6,886,419 B2
(45) Date of Patent: May 3, 2005

(54) MAIL PIECE FOR OBTAINING SAMPLES OF HARMFUL MATERIALS IN MAIL PROCESSING EQUIPMENT

(75) Inventors: Robert A. Cordery, Danbury, CT (US); Bertrand Haas, New Haven, CT (US)

(73) Assignee: Pitney Bowes Inc., Stamford, CT (US)

( * ) Notice: Subject to any disclaimer, the term of this patent is extended or adjusted under 35 U.S.C. 154(b) by 370 days.

(21) Appl. No.: 10/177,493

(22) Filed: Jun. 20, 2002

(65) Prior Publication Data

US 2003/0233891 A1 Dec. 25, 2003

(51) Int. Cl.[7] .................................................. G01N 1/00
(52) U.S. Cl. .................................................. 73/863.23
(58) Field of Search .................... 73/863.23, 863.71, 73/864, 864.31, 864.34, 864.35, 864.41, 864.51, 864.62, 864.71

(56) References Cited

U.S. PATENT DOCUMENTS

| | | | |
|---|---|---|---|
| 3,430,496 A | * | 3/1969 | Swanberg et al. ........ 73/864.71 |
| 4,350,507 A | | 9/1982 | Greenough et al. |
| 4,546,659 A | * | 10/1985 | Gill et al. ................. 73/864.62 |
| 4,829,812 A | * | 5/1989 | Parks et al. ................ 73/12.04 |
| 4,848,167 A | * | 7/1989 | Gordon et al. ............ 73/864.71 |
| 4,932,254 A | | 6/1990 | Davidson et al. |
| 5,420,403 A | | 5/1995 | Allum et al. |
| 5,571,976 A | * | 11/1996 | Drolet ..................... 73/864.71 |
| 5,607,497 A | | 3/1997 | Brown |
| 5,954,845 A | | 9/1999 | Willeke et al. |
| 5,971,391 A | | 10/1999 | Salomon et al. |
| 6,003,857 A | | 12/1999 | Salomon et al. |
| 6,135,441 A | | 10/2000 | Belec et al. |
| 6,176,428 B1 | | 1/2001 | Joseph et al. |
| 6,217,020 B1 | | 4/2001 | Supron et al. |
| 6,321,608 B1 | | 11/2001 | Wagner et al. |
| 6,328,300 B1 | | 12/2001 | Stefan et al. |
| 6,383,804 B1 | * | 5/2002 | Ward et al. .............. 435/309.1 |
| 6,446,514 B1 | * | 9/2002 | Danylewych-May et al. ....................... 73/863.21 |

* cited by examiner

*Primary Examiner*—Robert Raevis
(74) *Attorney, Agent, or Firm*—Alberta A. Vitale; Angelo N. Chaclas; George M. Macdonald

(57) ABSTRACT

The present invention is directed, in general to a mail piece and more particularly, a mail piece for collecting sample(s) of harmful materials from a mail processing device. The mail piece generally comprises: an air inlet, an air outlet and a collector. In an embodiment of the present invention, the mail pieces inlet is a material which causes sides of the mail piece to separate from one another when the mail piece is not under the pressure of a nip roller or similar grabbing device. In another embodiment of the present invention the collector is a filter present within the mail piece. In another embodiment of the present invention the collector is a filter or tacky material present inside the mail piece or on the out side of the mail piece. In another embodiment of the present invention, the mail piece is porous.

22 Claims, 3 Drawing Sheets

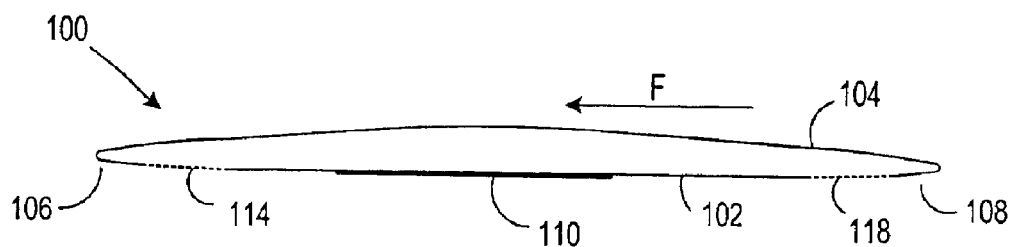
FIG. 1
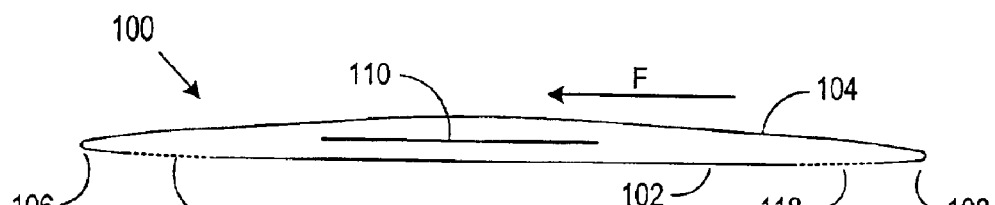
FIG. 2
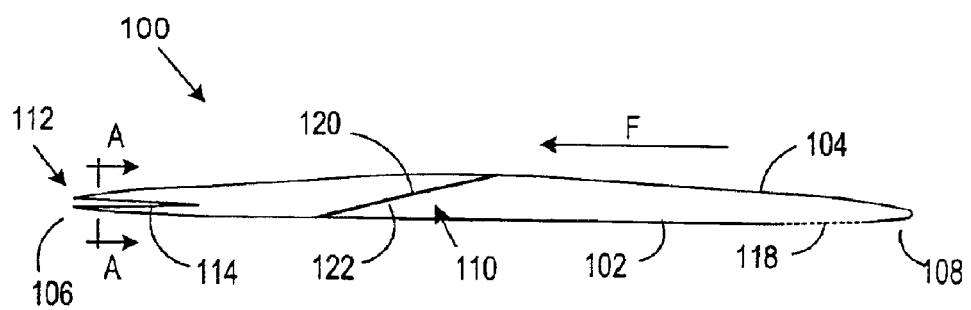
FIG. 3
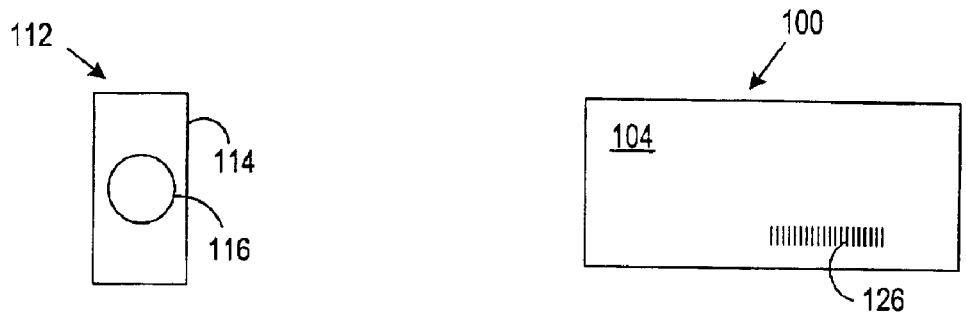
FIG. 3a
FIG. 6

MAIL PIECE FOR OBTAINING SAMPLES OF HARMFUL MATERIALS IN MAIL PROCESSING EQUIPMENT

FIELD OF THE INVENTION

The invention disclosed herein relates generally to mail pieces and more particularly, a mail piece that is used for hazardous material sampling.

BACKGROUND OF THE INVENTION

The United States accounts for the largest domestic letter traffic in the world, handling almost 200 billion pieces of mail each year. The United States Postal Service (USPS) employs more than 850,000 employees and operates more than 44,000 post offices throughout the country. In many respects, the economy of the country is dependent upon the postal system being able to efficiently and quickly deliver mail pieces. Any type of major disruption in the delivery of mail could have potentially serious detrimental effects on the country as a whole. In addition to the USPS, various services are used in the United States and other countries for delivery of mail to individuals and businesses to recipients to whom the sender does not want to deliver personally. These services include, for example, the United States Postal Service (USPS) and other courier services, e.g., Federal Express®, Airborne®, United Parcel Service,® DHL®, etc., hereinafter called "carriers". Unfortunately, sometimes the delivered materials may be illegal and/or hazardous to the health of the recipient and to the party who is delivering the goods, e.g., life-harming.

Soon after the Sep. 11, 2001 terrorist attack on the United States, someone and/or a group of people, has been adding harmful biological agents to the mail such as, for example, the spore-forming bacterium *Bacillus anthracis* (anthrax), within or on a mail piece. Such contaminants can be carried in several forms, including for example, a powder form. Other examples of life-harming materials are explosives; gun powder; blasting material; bombs; detonators; smokeless powder; radioactive materials; ammunition; atomic weapons; chemical compounds or any mechanical mixture containing any oxidizing and combustible units, or other ingredients in such proportions, quantities, or packing that ignite by fire, friction, concussion, percussion or detonation of any part thereof which may and is intended to cause an explosion; poisons; carcinogenic materials; caustic chemicals; hallucinogenic substances; illegal materials; drugs that are illegal to sell and/or dispense; and substances which, because of their toxicity, magnification or concentration within biological chains, present a threat to biological life when exposed to the environment, etc.

The harmful effects of only a few contaminated mail pieces can be far reaching, as cross-contamination of other mail pieces can easily occur when the mail pieces come in contact with each other or are passed through the same machines during processing. The addition of harmful biological agents to the mail submitted to the USPS has caused the death of some people and necessitated the closure of some post offices and other government office buildings and has caused delays in the processing and delivery of mail. The Centers for Disease Control and Prevention estimates that tens of thousands of mail pieces could have become cross-contaminated from only two contaminated mail pieces. The use of the postal system for such purposes has resulted in the need for a reliable way to detect small amounts of loose and possibly dangerous particulate matter present in mail processing machines so as to reduce the number of mail pieces that can become cross contaminated by the mail sorting machine by identifying the contamination early through testing. This will also reduce the number of contaminated mail pieces that are eventually opened by intended recipients.

Individuals who receive and handle mail are encouraged to use safety precautions such as: washing their hands thoroughly with soap and water after handling mail pieces; avoiding shaking mail pieces; avoiding bumping or sniffing mail pieces; and avoiding handling of mail pieces suspected of contamination. These measures can be impractical when the volume of mail is large. Thus, there is an urgent need to exclude or detect life-harming materials that contaminate mail processing equipment in such a way that the likelihood of cross contamination is reduced by timely sampling and detection.

Ideally, it would be desirous for the postal authority to examine and/or test each piece of mail individually for any possible contaminants before it enters the mail system, thereby isolating any contaminated mail pieces and preventing any cross-contamination. Such examination could be performed, for example, by visually inspecting each mail piece for a powdery substance contained therein. With the large volume of mail processed daily, however, the cost and time associated with visually inspecting each piece of mail makes such inspection unfeasible. It is imperative that any such testing and/or examination be capable of being performed both cost effectively and quickly to avoid delays in processing and delivering the mail.

Thus, there exists a need for a reliable way to quickly and cost effectively sample and/or detect small amounts of loose and possibly dangerous particulate matter in a mail processing equipment. There is an urgent need to sample and/or test the presence of life-harming materials that are included in the mail in such a way that cross contamination is reduced. One of the problems of the prior art is that a system is not available for sampling particulate matter present in mail processing equipment. Therefore, a device for sampling particulate matter in mail processing equipment is needed.

SUMMARY OF THE INVENTION

This invention overcomes the disadvantages of the prior art by providing a mail piece which can be used to collect sample(s) of material present in the feed path of a mail processing equipment. The detection of biohazardous material can help protect the intended recipients of mail pieces processed by the equipment from harm and also afford for less delays in mail piece processing. Early detection can reduce the occurrences of cross contamination.

The present invention is directed, in general to a mail piece and more particularly, a mail piece for collecting sample(s) of hazardous materials from a mail processing equipment. The mail piece generally comprises: an air inlet, an air outlet and a collector.

In an embodiment of the present invention, the mail piece's inlet causes the sides of the mail piece to separate from one another when the mail piece is not under the pressure of a nip roller or similar grabbing device. In another embodiment of the present invention the collector is a filter present within the mail piece. In another embodiment of the present invention the collector is a filter or tacky material present on the out side of the mail piece. In another embodiment of the present invention, the mail piece is porous.

An advantage of the present invention is that it provides a way to detect and thereby limit cross contamination of mail pieces during processing. The mail piece helps to decrease delays in the mail delivery caused by the presence of biohazardous material in mail pieces. Another additional advantage of the present invention is that the negative impact of delayed mail delivery is reduced. Other advantages of the invention will in part be obvious and will in part be apparent from the specification. The aforementioned advantages are illustrative of the advantages of the various embodiments of the present invention.

DESCRIPTION OF THE DRAWINGS

The above and other objects and advantages of the present invention will be apparent upon consideration of the following detailed description, taken in conjunction with accompanying drawings, in which like reference characters refer to like parts throughout, and in which:

FIG. 1 is a top view of an embodiment of a harmful material sampling mail piece.

FIG. 2 is a top view of an embodiment of a harmful material sampling mail piece.

FIG. 3 is a top view of another embodiment of a harmful material sampling mail piece.

FIG. 3a is a across section of an exemplary air inlet taken along line A—A of FIG. 3.

FIG. 6 is an illustration of a side of the mail piece, the side having identification information thereon.

DETAILED DESCRIPTION OF THE PRESENT INVENTION

Figure 4:
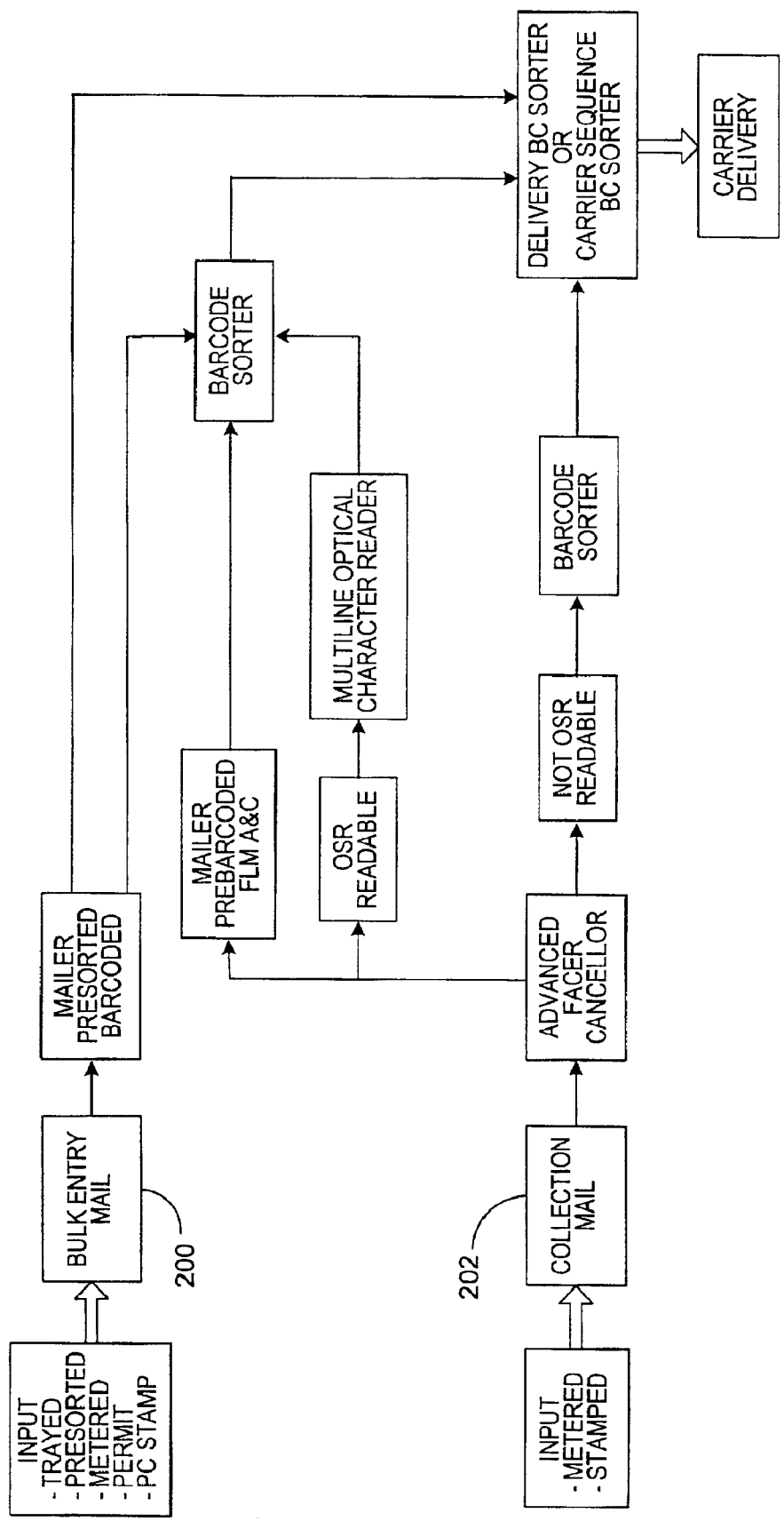
FIG. 4 is a block diagram of letter mail flow at the United States Postal Service.

In describing the present invention, reference will be made herein to FIGS. 1–5 of the drawings in which like numerals refer to like features of the invention. Features of the invention are not necessarily shown to scale in the drawings.

Mail Piece for Obtaining Samples of Harmful Materials in Mail Processing Equipment FIGS. 1–3 illustrate embodiments of the mail piece of the present invention for obtaining samples of harmful materials in mail processing equipment. The mail piece or harmful material sampling mail piece 100 generally comprises a first side 102, a second side 104, a first end 106 and a second end 108. Arrow F generally denotes the direction that the mail piece moves along a feed path F of mail sorting apparatus or other mail processing devices such as feeder 10 of FIG. 5 (described below).

FIG. 1 is a top view of an embodiment of a harmful material sampling mail piece 100. In this embodiment, a collector 110 is fixed to mail piece 100 on the first side (or outside) 102 of mail piece 100. The collector 110 can come in contact with various devices along feed path F of mail processing equipment such as equipment illustrated in FIGS. 4 and 5 (explained below). Through contact, samples of particulate matter can be obtained. The collector can be a tacky material to which particulate matter adheres. The tacky material could be for example, filter paper impregnated with oil and could be produced considering the following factors: smearing of information on the mail pieces, jamming caused by too much friction, slipping caused by not enough friction. The second side of mail piece 100 could include instructions (not shown) for controlling the processing of the mail piece 100 as it passes through mail processing equipment. The instructions could be in the form of a bar code 126 (shown in FIG. 6) such as a mail ID tag. An air inlet 114 could be positioned at the first end 106 of the mail piece 100 and substantially formed by at least a portion of at least one of the first and second sides 102, 104 of the mail piece 100. Thus, this portion of the mail piece that forms the air inlet 114 would be porous. Similarly, an air outlet 118 (shown with dashed lines) could be positioned at the second end 108 of the mail piece 100 and substantially formed by at least a portion of at least one of the first and second sides 102, 104 of the mail piece 100. Thus, this portion of the mail piece that forms the air outlet 118 would be porous. Alternately, in this embodiment and other embodiments, the air outlet 118 could be an opening in the mail piece formed by at least one of the first and second sides 102, 104 of the mail piece 100 at the second end 108 of the mail piece 100.

FIG. 2 is a top view of an embodiment of a harmful material sampling mail piece. In this embodiment, a collector 110 is positioned inside the mail piece 100. The second side 104 of mail piece 100 could include instructions (not shown) for controlling the processing of the mail piece 100 as it passes through mail processing equipment. The instructions could be in the form of a bar code (not shown) such as a mail ID tag. An air inlet 114 could be positioned at the first end 106 of the mail piece and substantially formed by at least a portion of at least one of the first and second sides 102, 104 of the mail piece 100. Thus, this portion of the mail piece that forms the air inlet 114 would be porous. Similarly, an air outlet 118 (shown in FIG. 2) could be positioned at the second end 108 of the mail piece 100 and substantially formed by at least a portion of at least one of the first and second sides 102, 104 of the mail piece 100. Thus, this portion of the mail piece that forms the air outlet 118 would be porous. Alternately, in this embodiment and other embodiments, the air outlet 118 could be an opening in the mail piece formed by at least one of the first and second sides 102, 104 of the mail piece at the second end 108 of the mail piece.

FIG. 3 is a top view of another embodiment of a harmful material sampling mail piece. The mail piece 100 generally comprises a first side 102, a second side 104, a first end 106 and a second end 108. Arrow F generally denotes the direction that the mail piece moves along a feed path F of mail sorting apparatus or other mail processing devices such as feeder 10 of FIG. 5 (described below). A third side 112, adjacent to the first and second sides 102, 104 of the mail piece 100 at the first end 106 of the mail piece forms an air inlet 114. In the preferred embodiment, the air inlet 114 is constructed of a material such as, for example a thin mil nylon or an engineered thermoplastic elastomer, that holds the first side 102 and second side 104 of mail piece 100 at a distance from one another. The material would also have spring-like properties so that mail processing devices such as, for example, the feeder 10 of FIG. 5, can nip the mail piece 100 with out permanently flattening the air inlet 114 and the air inlet 114 can open when the mail processing device releases its nip on the mail piece 100. The distances of separation between first side 102 and second side 104 can be up to the maximum thickness that mail processing equipment through which the mail piece 100 will be passed can accommodate without causing significant jamming problems. Such thickness can be determined by one of ordinary skill in the art. Also, the geometry of the first end 106 (or leading edge) of the mail piece 100 can be rounded or configured in such a way as to reduce the probability that the mail piece will jam on various structures such as the structures of feeder 10 shown in FIG. 5.

A cross section of a exemplary air inlet 114 taken along line A—A of FIG. 3 is shown in FIG. 3a. The third side 112 of mail piece 100 substantially forms the air inlet 114 and an opening 116 is formed by the third side 112 of mail piece 100 for allowing air to pass through the third side 112 and into mail piece 100. An air outlet 118 (shown in FIG. 3) could be positioned at the second end 108 of the mail piece 100 and substantially formed by at least a portion of at least one of the first and second sides 102, 104 of the mail piece 100. Thus, this portion of the mail piece 100 that forms the air outlet 118 would be porous. Alternately, in this embodiment and other embodiments, the air outlet 118 could be an opening 116 in the mail piece 100 formed by at least one of the first and second sides 102, 104 of the mail piece 100 at the second end 108 of the mail piece 100.

The embodiment of FIG. 3 also comprises a collector 110. The collector 110 comprises first side 120 and second side 122. Air (and particulate matter not shown) enter the mail piece 100 at air inlet 114 and travel to collector 110 first side 120 and exits collector 110 at second side 122. The air exiting collector 110 at the second side 122 travels to the air outlet 118. It is desirous that collector 110 capture at least a portion of the particulate matter in the air along the feed path of the mail processing device; depending upon the properties of the collector some particulate matter should be captured by the collector. The properties of the collector 110 can be determined by one of ordinary skill in the art by evaluating the type of particulate matter that is desired to be collected and choosing an appropriate collector for the particulate matter.

The mail piece could be passed through mail processing equipment at various entry points such as bulk mail entrance 200 or collection mail entrance 202 shown in FIG. 4. Other entry points deemed appropriate by an operator facilitating collection using the mail piece 100 of the present invention could be used. The mail piece 100 could be addressed to a test facility which would test the particulate matter captured by collector 110. The address of the test facility could be positioned on one of the first or second sides 102, 104 of the mail piece 100. The mail piece 100 could travel through more than one postal processing facility and such information could be associated with the mail piece ID tag described above. The mail piece 100 could alternately be passed through processing equipment and obtained by an operator and placed in a container. The container could be delivered to the test facility or picked up for delivery to test facility. If possible, depending upon factors such as, for example, the complexity of the testing and the apparatus needed for testing, the testing could be performed at the postal facility.

The collector 110 could be a filter specifically designated to filter a particular type of harmful material. The determination of the type of collector 110 could be made by considering factors such as, for example, space available for placement of the filter on or in the mail piece 100, the size of the particles to be filtered, the thickness of the filter (evaluating the thickness that mail piece processing devices can handle without or with low probability of jamming), availability and cost. As an example, the collector 110 could be a filter that can capture Anthrax spores. The U.S. Center for Disease Control states that the typical particle size of an Anthrax spore (which is an aerosol) is estimated to be 2–6 microns. Therefore, if the collector 110 was designated to collect Anthrax spores, an appropriate filter able to collect spores that measure 2–6 microns would be needed. There are many commercially available filter materials that can be used to filter Anthrax. These commercially available products would need to be produced to meet the construction requirements for mail piece 100 collector 110. One example of a commercially available filter that advertises the ability to filter Anthrax is the BIOGUARD™ FILTER offered by Con-Aire Industries Incorporate of Smyrna, Ga. The filter is constructed polyester medias that are woven to different densities to strain out the contaminants such as Anthrax. While BIOGUARD™ FILTER is commercially available for heating and air conditioning systems, similarly constructed products could be used for collector 110. Commercially available aerosol filtering can also be used.

Automated Mail Piece Feeding & Sorting Overview

The mail piece 100 of the present invention can be passed through mail processing equipment such as, for example, mail feeding equipment, mail sorting equipment including various mail handling equipment used at postal sorting facilities. FIG. 4 is a simplified block diagram of letter mail flow at a postal sorting facility such as, for example a United States Postal Service postal sorting facility. The mail piece 110 of the present invention could enter the letter mail flow at any number of physical entrances in the diagram. The determination as to where the mail piece 110 could enter the mail flow could be made considering factors including, but not limited to, from what particular piece of mail feeding equipment is it desired to have a sample collected there from.

Figure 5:
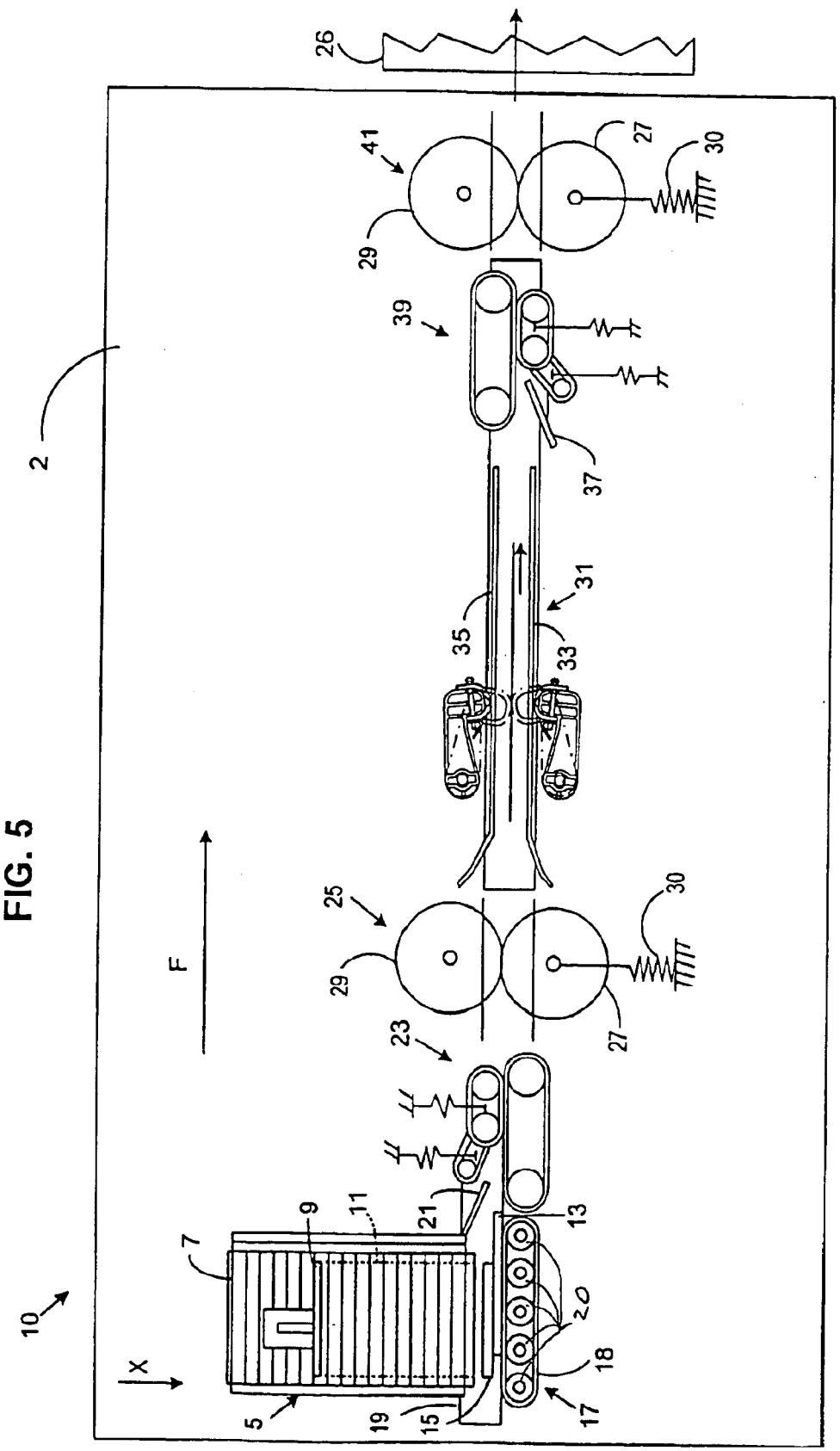
FIG. 5 is an exemplary schematic top plan view of a mail feeder incorporating nip or takeaway rollers which can be used to squeeze the sampling mail piece of the present invention.

FIG. 5 is a schematic top plan view of a mail feeder incorporating nip or takeaway rollers 27, 29 which can be used to squeeze the sampling mail piece of the present invention. Feeder 10 is an example of some of the various paper handling devices that can be included along the feed path of a mail sorting apparatus. Mail piece sorting equipment can typically sort mail pieces of varying sizes. Various devices are included in mail sorting equipment including roller devices which can nip the mail pieces and move the mail pieces along a feed path in the mail sorting apparatus. The feeder 10 of mail piece sorting apparatus is designed to feed mail pieces of varying sizes, thicknesses and finishes and therefore, can singulate and feed variously configured mail pieces including, for example, envelopes of various sizes, mail pieces of various thickness thick, magazines, variously configured small packages, and the mail piece 100 of the present invention.

FIG. 5 shows a feeder 10 of a mail sorting apparatus. The feeder 10 has conventional framework 2 upon which all of the components of the feeder 10 are mounted. Feeder 10 includes a stack advance mechanism 5 having a continuous conveyor belt 7 mounted for rotation in a conventional manner about a plurality of pulleys (not shown) in the direction of arrow "X". Mounted on the conveyor belt 7 in a conventional manner is an upstanding panel 9 which moves with the conveyor 7 in the direction of arrow "X". In operation, a stack of mail 11 is placed on the conveyor belt 7 and rests against the panel 9. The stack of mixed mail includes a lead mail piece 13 and a second mail piece 15. Thus, as the conveyor belt 7 is set into movement, the stack of mixed mail 11 is moved toward an input feed structure 17. Input feed structure 17 includes a belt 18 which is driven into rotation about a series of pulleys 20, at least one of which is a driven pulley. Accordingly, as the stack advance mechanism 5 forces the lead mail piece 13 into contact with the belt 18, the lead mail piece 13 is laterally moved away from stack of mixed mail 11. Additionally, a driven belt 19 which makes contact with the bottom edge of the lead mail piece 13 also assists in moving the lead mail piece 13 downstream past a guide mechanism 21 and toward a first document singulating apparatus 23. As shown, the combination of the stack advance mechanism 5, the input feed structure 17, and the guide plate 21 help to present the mail pieces which are removed from the stack of mixed mail 11 into the first document singulating apparatus 23 in a shingled manner. The first document singulating apparatus 23 operates to separate the lead mail piece 13 from the remaining stack of mixed mail 11 so that only individual mail pieces are presented to output feeding structure 25 for ultimate processing downstream to a processing station 26 where each individual mail piece has some type of operation (printing, scanning, etc.) performed thereon.

Output feeding structure 25 includes a take away rollers 27 and 29 which receive the mail piece as it exits the first document singulating apparatus 23 and helps to transport it downstream. The take away rollers comprise a drive roller 29 and an idler roller 27. The take away idler roller 27 is spring loaded by spring 30 and is moveable toward and away from the take away drive roller 29 to accommodate different mail piece thicknesses. An a aligner station 31 consisting of two guide walls 33, 35 which help to direct the individual mail pieces in a vertical fashion to ensure that they are aligned on their bottom edge prior to transport past a second guide plate 37 and into a second document singulating apparatus 39. Subsequent to passage through the second document singulating apparatus 39, the individual mail pieces are transported into a second set of take away rollers 41 which transport the individual mail pieces to the processing station 26. The second set of takeaway rollers 41 has the same structural components as the first set of take away rollers 25.

The second singulating apparatus 39 has the same structural components as the first singulating apparatus 23 and can be driven by an independent drive system similar to that used for first singulating apparatus 23. The use of the redundant singulating apparatus structure improves the reliability of separating individual documents from each other since, if a multi-feed does pass through the first singulating apparatus 23 it is likely that the second singulating apparatus 39 will effectively separate the documents of a multi-feed.

Exemplary aspects of the feeder 10 that can be used for feeding the mail piece 100 of the present invention are disclosed in the following: U.S. Pat. No. 5,971,391, issued Oct. 26, 1999 to Salomon et al. titled NUDGER FOR A MAIL HANDLING SYSTEM; U.S. Pat. No. 6,003,857, issued Dec. 21, 1999 to Salomon et al. titled SINGULATING APPARATUS FOR A MAIL HANDLING SYSTEM, U.S. Pat. No. 6,135,441 issued Oct. 24, 2000 to Belec et al. titled TWO STAGE DOCUMENT SINGULATING APPARATUS FOR A MAIL HANDLING SYSTEM; U.S. Pat. No. 6,217,020 issued Apr. 17, 2001 to Supron et al. titled METHOD AND APPARATUS FOR DETECTING PROPER MAIL PIECE POSITION FOR FEEDING; and U.S. Pat. No. 6,328,300 issued Dec. 11, 2001 to Stefan et al. titled ALIGNER MECHANISM FOR A MAIL HANDLING SYSTEM and assigned to the assignee of the present invention and incorporated by reference herein.

The mail piece 100 of the present invention could enter feeder 10 illustrated in FIG. 5 by way of placement in stack 11, placement into aligner station 31 and processed through nip rollers 27, 29. The nip rollers 27, 29 can depress the air inlet 114 (of FIG. 3) and the air inlet 114 can re-open once it is released from the nip of rollers 27, 29. The mail piece 100 can then be collected at a down stream end such as down stream processing devices (generally denoted as 26 in FIG. 5) for subsequent testing.

The present invention provides a system and method for helping to deter delays in the mail delivery. Another additional advantage of the present invention is that the negative impact of delayed mail delivery is reduced. It further provides the ability to protect recipients against receipt of life threatening mail pieces. While the present invention has been disclosed and described with reference to a single embodiment thereof, it will be apparent, as noted above that variations and modifications may be made therein. It is, thus, intended in the following claims to cover each variation and modification that falls within the true spirit and scope of the present invention.

What is claimed is:

1. A mail piece having first and second sides and first and second ends, the mail piece comprising:
    an air inlet positioned at a first end of the mail piece, the air inlet for intaking air along the feed path of a mail processing device;
    an air outlet positioned at a second end of the mail piece distal to the air inlet for outleting air that travels through the mail piece from the air inlet to the air outlet;
    a collector, the collector part of the mail piece positioned so as to collect hazardous material along the feed path of the mail processing device.

2. The mail piece as claimed in claim 1 wherein the air inlet is substantially formed by at least a portion of at least one of the first and second sides of the mail piece.

3. The mail piece as claimed in claim 1 wherein the air outlet is substantially formed by at least a portion of at least one of the first and second sides of the mail piece.

4. The mail piece as claimed in claim 3 wherein the air outlet comprises the collector.

5. The mail piece as claimed in claim 1 wherein the air outlet comprises at least one opening formed by the at least one of the first and second sides of the mail piece.

6. The mail piece as claimed in claim 1 further comprising a third side adjacent to the first and second sides at the first end of the mail piece whereby the third side forms the air inlet.

7. The mail piece as claimed in claim 6 whereby the air inlet comprises an opening formed by the third side of the mail piece.

8. The mail piece as claimed in claim 1 whereby the air inlet comprises the collector.

9. The mail piece as claimed in claim 6 wherein the collector comprises a porous material having a first and second side and whereby air enters the mail piece through the air inlet and travels to and enters the collector at the first side and exits the collector at the second side and travels to the at least one air outlet.

10. The mail piece as claimed in claim 1 wherein the air inlet comprises a rigid material which causes a third side of the mail piece to hold the first and second sides of the mail pieces at a distance from one another, the rigid material having some resilience so that mail handling apparatus can nip the mail piece with out permanently flattening the air inlet and the air inlet can open when the mail handling apparatus releases the nip on the mail piece.

11. The mail piece as claimed in claim 9 wherein the air inlet comprises a material which allows the third side of the mail piece to hold the first and second sides of the mail pieces at a distance from one another, the material having properties that allow the mail processing device to nip the mail piece and temporarily flatten the air inlet and the air inlet can open when the mail processing device releases the nip on the mail piece.

12. The mail piece as claimed in claim 1 whereby the mail piece is passed through the mail processing device to capture a sample of particulate matter along the feed path of the mail processing device.

13. The mail piece as claimed in claim 1 further comprising an identification mark, the identification mark including at least one piece of information from the group consisting of: an identification of a mail processing device, a mail sorting facility identification, and a time of processing identification.

14. The mail piece as claimed in claim 1 further comprising addressee information indicative of a testing facility whereby the mail piece can be delivered to the test facility identified in the addressee information.

15. The mail piece as claimed in claim 14 wherein the addressee information is readable by the mail processing device.

16. The mail piece as claimed in claim 14 wherein the addressee information is readable by an operator.

17. The mail piece as claimed in claim 1 whereby the collector is positioned on at least one of the first and second sides of the mail piece.

18. The mail piece as claimed in claim 17 whereby the collector comprises a tacky material.

19. The mail piece as claimed in claim 1 whereby the collector is positioned in a space defined by the first and second sides of the mail piece and the mail piece comprises a porous material through which hazardous material may pass.

20. The mail piece as claimed in claim 19 whereby the collector is adhered to at least a portion of the first and second sides of the mail piece, between the air inlet and the air outlet.

21. A mail piece having first and second sides, the mail piece comprising:

a collector, the collector part of the mail piece positioned on at least one of the first and second sides so as to collect hazardous material along the feed path of a mail processing device.

22. The mail piece as claimed in claim 21 wherein the collector is a tacky material.

* * * * *